(12) United States Patent
Amini et al.

(10) Patent No.: US 8,260,034 B2
(45) Date of Patent: Sep. 4, 2012

(54) MULTI-MODAL DATA ANALYSIS FOR DEFECT IDENTIFICATION

(75) Inventors: Lisa Amini, Yorktown Heights, NY (US); Brian Christopher Barker, Poughkeepsie, NY (US); Perry G. Hartswick, Millbrook, NY (US); Deepak S. Turaga, Nanuet, NY (US); Olivier Verscheure, Hopewell Junction, NY (US); Justin Wai-chow Wong, South Burlington, VT (US)

(73) Assignee: International Business Machines Corporation, Armonk, NY (US)

( * ) Notice: Subject to any disclaimer, the term of this patent is extended or adjusted under 35 U.S.C. 154(b) by 1169 days.

(21) Appl. No.: 12/017,779

(22) Filed: Jan. 22, 2008

(65) Prior Publication Data

US 2009/0185739 A1    Jul. 23, 2009

(51) Int. Cl.
*G06K 9/00* (2006.01)
*G06F 17/50* (2006.01)
*H01L 21/00* (2006.01)

(52) U.S. Cl. ........ 382/145; 382/141; 382/144; 382/147; 382/148; 382/149; 382/151; 716/51; 716/52; 716/53; 438/5.7

(58) Field of Classification Search ............... 382/145, 382/141, 144, 147, 148, 149, 151; 716/51, 716/52, 53; 438/5, 7
See application file for complete search history.

(56) References Cited

U.S. PATENT DOCUMENTS

| 5,161,110 | A |   | 11/1992 | Dorchak |
| 5,239,456 | A |   | 8/1993 | Badavas et al. |
| 5,606,251 | A | * | 2/1997 | Ryle et al. ............... 324/750.01 |
| 5,761,064 | A | * | 6/1998 | La et al. ..................... 700/110 |
| 5,913,105 | A | * | 6/1999 | McIntyre et al. ............. 438/16 |
| 6,442,445 | B1 |   | 8/2002 | Bunkofske et al. |
| 6,456,899 | B1 |   | 9/2002 | Gleason et al. |
| 6,563,300 | B1 | * | 5/2003 | Jackson et al. ........... 324/750.15 |
| 6,584,368 | B2 |   | 6/2003 | Bunkofske et al. |
| 6,590,519 | B2 | * | 7/2003 | Miceli et al. .................... 342/22 |
| 6,658,640 | B2 |   | 12/2003 | Weed |

(Continued)

OTHER PUBLICATIONS

Elias-Fuste, et al. "Constant False Alarm Rate for a Radar Data Fusion Center with N Parallel Distributed Cell Averaging Receivers." Radar Conference, 1990., Record of the IEEE 1990 International . (1990): 507-510. Print.*

(Continued)

*Primary Examiner* — Matthew Bella
*Assistant Examiner* — Michael A Newman
(74) *Attorney, Agent, or Firm* — William Stock; Ryan, Mason & Lewis, LLP

(57) ABSTRACT

A technique for identifying a defect in an object produced by a controllable process. A first type of data generated as a result of production of the object by the controllable process is obtained. A second type of data generated as a result of production of the object by the controllable process is obtained. The first type of data and the second type of data are jointly analyzed. A defect is identified in the object based on the joint analysis of the first type of data and the second type of data. By way of example, the controllable process comprises a semiconductor manufacturing process such as a silicon wafer manufacturing process and the object produced by the semiconductor manufacturing process comprises a processed wafer. The first type of data comprises tool trace data and the second type of data comprises wafer image data. The tool trace data is generated by a photolithographic tool.

1 Claim, 5 Drawing Sheets

U.S. PATENT DOCUMENTS

| | | | |
|---|---|---|---|
| 6,678,569 B2 | 1/2004 | Bunkofske et al. | |
| 6,740,534 B1 * | 5/2004 | Adams et al. | 438/14 |
| 6,826,298 B1 | 11/2004 | O'Dell et al. | |
| 6,980,873 B2 | 12/2005 | Shen | |
| 7,062,417 B2 | 6/2006 | Kruger et al. | |
| 7,099,729 B2 | 8/2006 | Tai et al. | |
| 7,200,455 B2 * | 4/2007 | Schulze | 700/109 |
| 7,277,824 B1 * | 10/2007 | Ryskoski et al. | 702/185 |
| 7,337,034 B1 * | 2/2008 | Lensing et al. | 700/121 |
| 7,634,383 B2 * | 12/2009 | Engel et al. | 702/181 |
| 7,684,887 B2 * | 3/2010 | Behrisch et al. | 700/110 |
| 2003/0168429 A1 * | 9/2003 | Lai et al. | 216/59 |
| 2003/0216887 A1 | 11/2003 | Shieh | |
| 2005/0033550 A1 | 2/2005 | Macaluso et al. | |

OTHER PUBLICATIONS

Koushanfar, et al. "On-line Fault Detection of Sensor Measurements." IEEE Sensors. (2003): 974-980. Print.* de Vries, et al. "On the False-Positive Rate of Statistical Equipment Comparisons Based on the Kruskal-Wallis H Statistic." IEEE Transactions on Semiconductor Manufacturing. 20.3 (2007): 286-292. Print.*

P. Domingos et al., "Mining High-Speed Data Streams," Proceedings of the sixth ACM SIGKDD international Conference on Knowledge Discovery and Data Mining, 2000, 10 pages.

G. Qu et al., "Wafer Defect Detection Using Directional Morphological Gradient Techniques," EURASIP Journal on Applied Signal Processing, 2002, pp. 686-703, vol. 7.

M. Rencher et al., "Design-Aware Verification of Layout Patterning," Design for Yield, http://www.mentor.com/products/dft/news/articles/upload/inside_eedesign7.pdf, pp. 43-46, (2004).

A. Skumanich et al., "Advanced Interconnect Process Development Utilizing Wafer Inspection with "On-the-Fly" Automatic Defect Classification," IEEE/SEMI Advanced Semiconductor Manufacturing Conference, 1999, pp. 259-264.

T. Bearda et al., "The Effect of Backside Particles on Substrate Topography,"Japanese Journal of Applied Physics, 2005, pp. 7409-7413, vol. 44, No. 10.

* cited by examiner

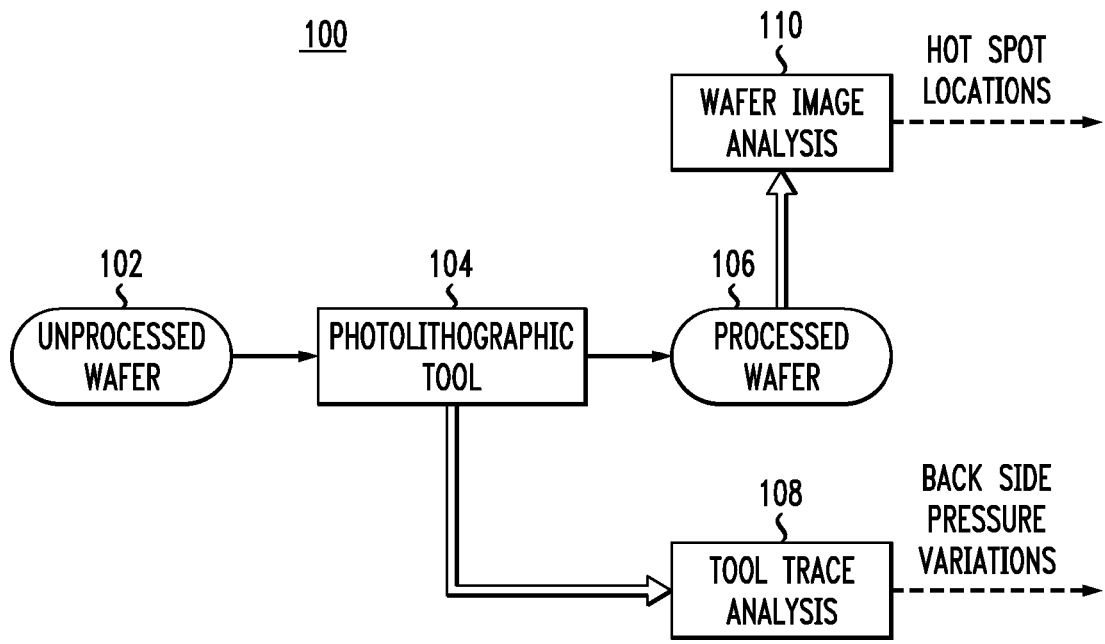
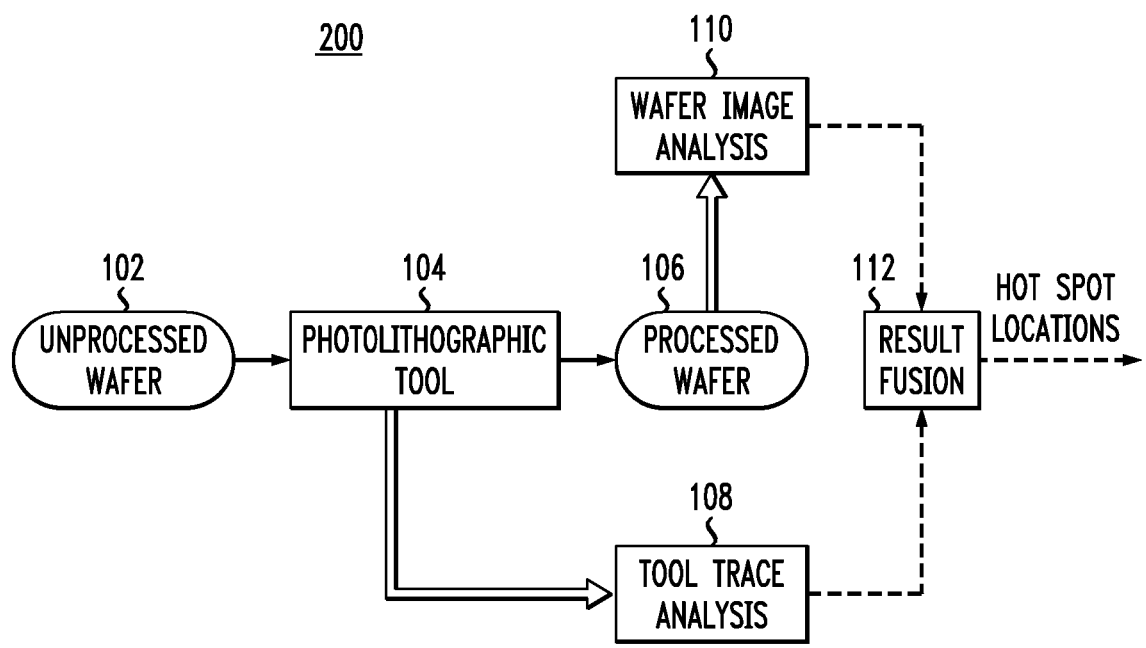

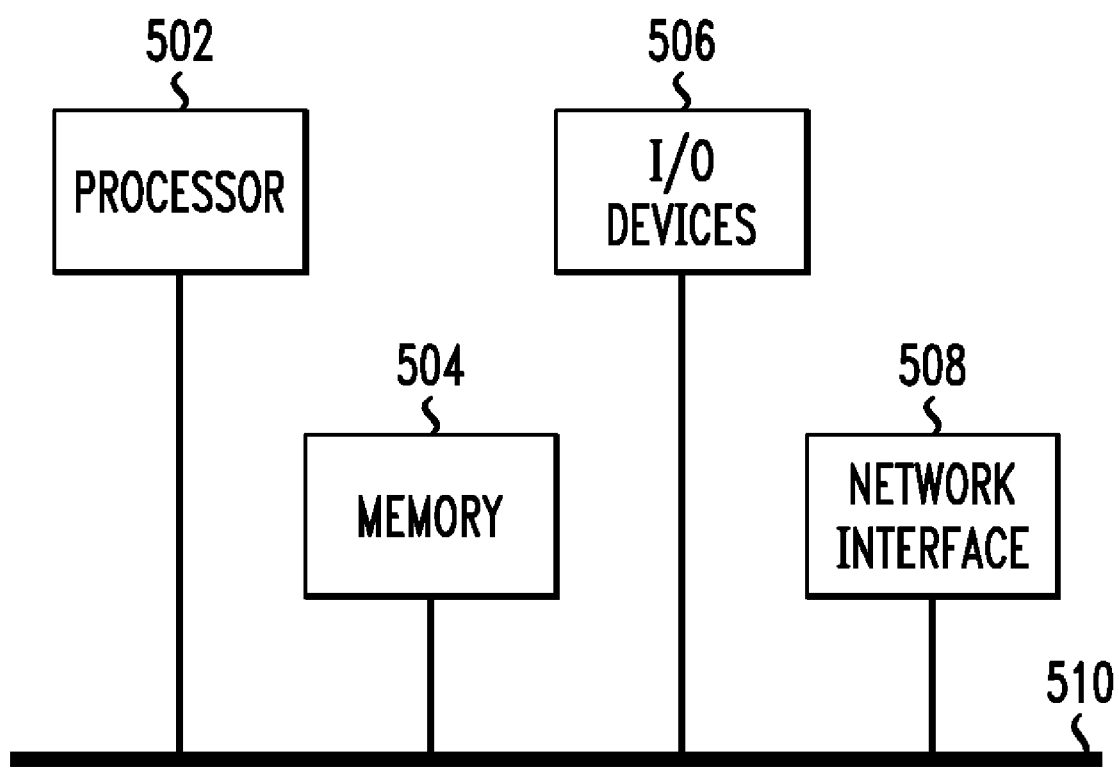

MULTI-MODAL DATA ANALYSIS FOR DEFECT IDENTIFICATION

FIELD OF THE INVENTION

The present invention relates to defect identification and, more particularly, to multi-modal analysis for use in such defect identification.

BACKGROUND OF THE INVENTION

Defects in the semiconductor wafer fabrication process may occur due to several operational, mechanical or chemical control errors, or due to environmental uncertainty. It is often very difficult to even identify (detect and classify) different defects on a wafer, and consequently even more difficult to determine which process steps (or combination thereof) or devices cause these defects. Automated defect analysis consists of two different types of tests, a set of inline defect analysis tests, and a set of offline analysis tests. The inline tests are performed after specific processing steps to capture the impact of the processing on the wafer, and data and results for these tests are available in near real time. On the other hand, offline tests include comprehensive electrical tests that determine the actual wafer yield and are performed after several processing steps, with results available only several hours/days after the actual wafer processing.

Example of inline tests (inspection) include After Development Inspection (ADI) and After Etch Inspection (AEI), which are performed specifically after the photolithography process, and the etch process, respectively. ADI involves imaging the wafer (with approximately 18 micron resolution color images) and analyzing these images to identify and classify defects. Analysis during ADI may include several image processing/machine vision techniques to identify the spatial image features (such as swirls, loops, etc) corresponding to specific wafer defects. These algorithms need to operate on large volumes of image data generated, in near real time. Based on these inspection results, higher resolution images are captured with a Scanning Electron Microscope (SEM) and these are analyzed by human operators. Improving the accuracy of automatic defect identification during analysis of ADI images is essential to minimize the cost of human intervention, and to improve throughput.

At the same time, tool trace data is also collected from individual processing tools to monitor their operation. Tool trace data consists of time series of the tool parameters, such as temperature, pressure, chemical composition, collected when wafers are being processed. Automated analysis of these tool trace parameters is used to characterize tool operation as normal or out-of-specification. These tool trace parameters may also be used to predict wafer yield, especially when the tool operation is responsible for creating defects on wafers. However, there are often a large number of observable tool trace parameters, collected at multiple time steps, and analyzing this data in near real time, especially for high-volume tools such as photolithography tools is very difficult. Furthermore, there are often dynamic variations in the tool parameters, requiring recalibrating any models or analysis online to maintaining accuracy of the derived results.

SUMMARY OF THE INVENTION

Principles of the invention provide multi-modal analysis for use in identifying a defect in an object produced by a controllable process.

By way of example, in a first aspect of the invention, a method for identifying a defect in an object produced by a controllable process comprises the following steps. A first type of data generated as a result of production of the object by the controllable process is obtained. A second type of data generated as a result of production of the object by the controllable process is obtained. The first type of data and the second type of data are jointly analyzed. A defect is identified in the object based on the joint analysis of the first type of data and the second type of data.

The controllable process may be adjustable based on the joint analysis of the first type of data and the second type of data. The joint analysis step may further comprise combining results of a first type of analysis of the first type of data and results of a second type of analysis of the second type of data. The joint analysis step may further comprise using results of a first type of analysis of the first type of data to affect a second type of analysis of the second type of data.

In one embodiment, the controllable process comprises a semiconductor manufacturing process such as a silicon wafer manufacturing process and the object produced by the semiconductor manufacturing process comprises a processed wafer. The first type of data comprises tool trace data and the second type of data comprises wafer image data. The tool trace data is generated by a photolithographic tool.

In a second aspect of the invention, an article of manufacture for identifying a defect in an object produced by a controllable process comprises a computer readable storage medium including one or more programs which when executed by a computer perform the above described obtaining, joint analysis and defect identifying steps.

In a third aspect of the invention, apparatus for identifying a defect in an object produced by a controllable process comprises: a memory; and a processor coupled to the memory and operative to: (i) obtain a first type of data generated as a result of production of the object by the controllable process; (ii) obtain a second type of data generated as a result of production of the object by the controllable process; (iii) jointly analyze the first type of data and the second type of data; and (iv) identify a defect in the object based on the joint analysis of the first type of data and the second type of data.

In a fourth aspect of the invention, a system for controlling a controllable process that produces an object comprises: one or more analyzers coupled to the controllable process and configured to: (i) obtain a first type of data generated as a result of production of the object by the controllable process; (ii) obtain a second type of data generated as a result of production of the object by the controllable process; (iii) jointly analyze the first type of data and the second type of data; and (iv) identify a defect in the object based on the joint analysis of the first type of data and the second type of data; wherein the controllable process is adjustable based on the joint analysis of the first type of data and the second type of data.

These and other objects, features and advantages of the present invention will become apparent from the following detailed description of illustrative embodiments thereof, which is to be read in connection with the accompanying drawings.

BRIEF DESCRIPTION OF THE DRAWINGS

FIG. 1 illustrates an environment wherein multi-modal data analysis according to embodiments of the invention may be implemented.

FIG. 2 illustrates a multi-modal data analysis methodology for performing independent data analysis with result fusion, according to an embodiment of the invention.

FIG. 5 illustrates a computer system wherein techniques for performing multi-modal data analysis may be implemented according to an embodiment of the invention.

DETAILED DESCRIPTION OF PREFERRED EMBODIMENTS

Figure 3A:
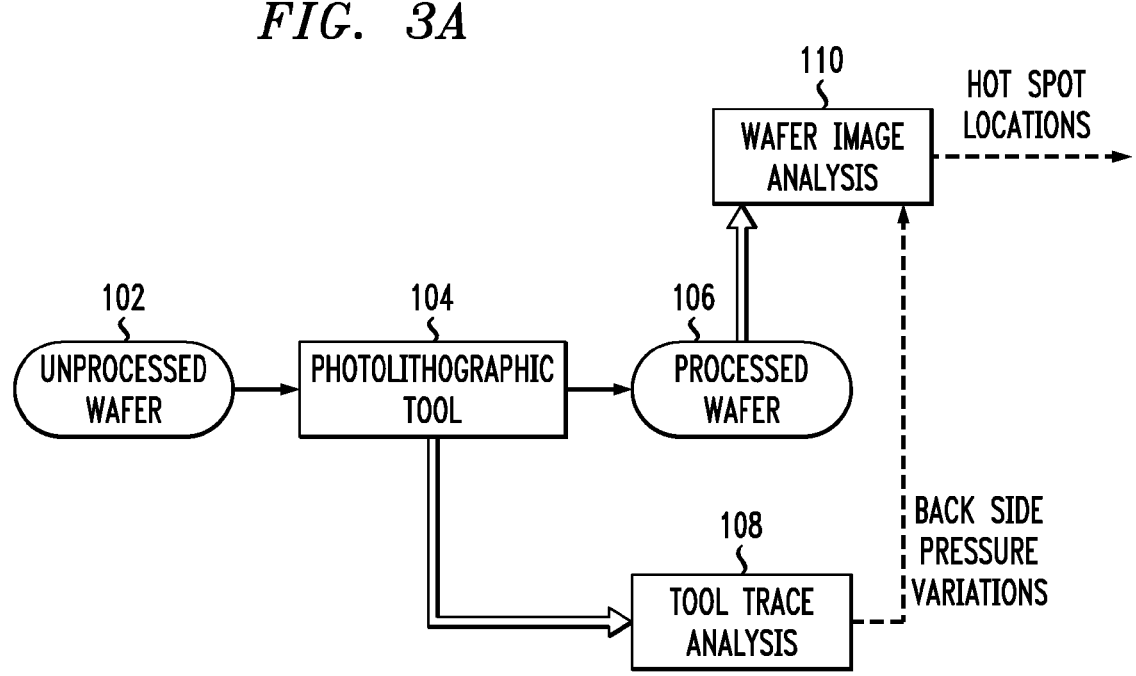
FIG. 3A illustrates a multi-modal data analysis methodology for using tool trace data analysis to drive wafer image analysis, according to an embodiment of the invention.

Illustrative embodiments of the invention will be described below in the context of a controllable process such as a semiconductor manufacturing (wafer fabrication wherein the "object" produced is a processed wafer) process involving After Development Inspection (ADI) and photolithography. However, it is to be understood that the principles of the invention are not limited thereto and may be used in techniques other than ADI and photolithography. It should also be understood that the invention is not limited to the particular materials, features, processing steps, and applications shown and described herein.

In accordance with principles of the invention, we propose to perform joint analysis across multiple data modalities (in this specific embodiment, ADI images and photolithography tool trace parameters) using near real-time streaming analytics to improve the accuracy of early fault detection and classification (i.e., defect identification), to assist human operators in inspection, to improve wafer yield prediction, and to ultimately drive automated process control. Some advantages of such a joint analysis include:

(i) Improved accuracy for wafer defect detection and yield prediction. By fusing results from these different sources, we can improve any predictions of wafer yield and tool operation characteristics.

(ii) Complexity adaptive processing. We can adaptively vary the wafer image analysis complexity, given results of analysis from tool trace parameters, e.g., when we know that the tool is operating normally, we may reduce the complexity of the wafer image processing algorithms. Similarly, through hierarchical processing of the data, and reuse of results, we can also deal with the large data volumes of trace data. This can allow us to develop Fault Detection and Classification (FDC) schemes for photolithography tools.

(iii) Sensitivity analysis. By correlating these different data types, we can quantify the impact of different tool parameters on the wafer defects, and use this to identify the most relevant tool parameters that need to be monitored. This can be also used to drive the development of models for tool behavior.

As an exemplary embodiment of the invention, we consider a specific type of wafer defect that may be created during the photolithographic process, and may be observed both using the ADI image, as well as using some tool trace parameters. During the processing inside the tool, the wafer sits on a chuck where foreign particles may be introduced on the wafer surface. These foreign particles may have sizes typically within the sub-micron range, although it is possible to have particles that are large enough to be visible to the naked eye. The presence of these particles impacts the processing and resultant wafer yield significantly.

The defects created are often captured by the ADI images as hot-spots. There are several well-known image processing techniques used to detect hot spots on wafers and they include morphological analysis with directional dilation, or comparing the obtained image with a simulated image for the three dimensional resist profile using lithography simulators. These different techniques are computationally expensive, and often have classification accuracy for hot spots of around 75%.

At the same time, the presence of foreign particles on the wafer may manifest itself in a pressure differential in the measured back side pressure (i.e., a tool trace parameter). Hence, by looking at the variation of this pressure differential across different regions, it is possible to identify the potential presence of foreign particles, and their location on the wafer surface. An existing approach uses topographical information to determine whether the chuck is the source of localized elevation, and resulting defocus.

FIG. 1 illustrates an environment 100 wherein analysis of the two different data types may be implemented. As shown, unprocessed wafer 102 is subjected to photolithography tool 104 to generate processed wafer 106. As is well known, photolithography is the process of transferring geometric shapes on a mask to the surface of a silicon wafer.

In a first data type, tool trace parameters that were collected and stored during the photolithography process are analyzed in tool trace analyzer 108. Tool trace analyzer 108 detects the variation of the pressure differential across different regions and thus identifies the potential presence of foreign particles, and their location on the wafer surface.

In a second data type, one or more images of processed wafer 106 are captured and the image data is analyzed by wafer image analyzer 110. Wafer image analyzer 110 applies image processing techniques that detect hot spot locations, which correspond to defects in the processed wafer.

We now provide three examples of performing a joint or multi-modal analysis of these different data types.

FIG. 2 illustrates a multi-modal data analysis methodology 200 for performing independent data analysis with result fusion, according to an embodiment of the invention.

As shown, results of after image analysis 110 and tool data analysis 108 are combined in result fusion unit 112 to improve accuracy of hot spot detection. In this embodiment, the two different analyses are performed independently, but the results from the two are fused (combined) to improve the confidence of the wafer hot spot detection. This allows a loose coupling between the data, but can result in improved accuracy.

By way of example, consider two independent classifiers—a classifier that detects defects using backside pressure differential from the tool trace (box 108 in FIG. 2), and an image-based classifier (box 110 in FIG. 2). Consider that the two classifiers have operating points characterized by their individual probabilities of detection $p_D^1$ and $p_D^2$, and probabilities of false alarm $p_F^1$ and $p_F^2$. Consider that the result fusion box involves combining results such that it passes only those wafers that are labeled defective by both classifiers. Then the resulting fused output has probabilities of detection and false alarm $p_D^{Fused}$ and $p_F^{Fused}$. When the two classifiers, whose results are fused, are independent, we may compute these fused probabilities as:

$$p_D^{Fused}=p_D^1 p_D^2 \text{ and } p_F^{Fused}=p_F^1 p_F^2. \qquad 5$$

Since the independent classifiers have $p_D^i > p_F^i$, the fusion results in reducing the false alarm probability significantly, while sacrificing the probability of detection to a small degree. As a numerical example, consider the case when $p_D^1=0.99$, $p_F^1=0.3$ and $p_D^2=0.9$, $p_F^1=0.1$, i.e., classifier 1 catches 99% of defects but also has a false alarm rate of 30% while classifier 2 catches 90% of defects but has a lower false alarm rate of 10%. The new resulting classifier will have $p_D^{Fused}=0.891$ and $p_F^{Fused}=0.03$, i.e., close to 90% detection with only 3% false alarms.

Note that other types of result fusion are possible, and those can result in different tradeoffs between the resulting probability of detection and false alarm.

FIG. 3A illustrates a multi-modal data analysis methodology for using tool trace data analysis to drive wafer image analysis, according to an embodiment of the invention. Since the photolithographic tool trace data analysis 108 is likely to be less computationally complex than the wafer image data, we realized that the results of this analysis (in terms of parameters variations, trends, anomalies, etc.) can be communicated to the wafer image analysis 110, and used to adaptively analyze the image.

For instance if the back-side pressure differential is detected to be high for some regions, the wafer image analysis should focus more computational resources on those likely predicted locations than uniformly across the entire image. This can result in significantly reduced computational complexity for the wafer image analysis, as well as improve the accuracy of any detected results.

By way of example, consider the classifiers in FIG. 3A—a classifier that detects defects using backside pressure from the tool trace (box 108 in FIG. 3A), and an image-based classifier (box 110 in FIG. 3A). Consider that the image-based classifier uses morphological analysis to detect spatial structures and defects on the wafer image. Mathematical morphology is a well-known set theory approach (developed by Serra in 1982). Based on a formal mathematical framework, mathematical morphology provides an approach to the processing of digital images that is based on geometrical shape. Morphological analysis is computationally expensive with the complexity scaling roughly linearly with the number of pixels (resolution) in the image (e.g., the complexity increases about 4 times when the image resolution is increased to 352×288 from 176×144). Correspondingly, the accuracy of the detection increases with the resolution. Now consider that the wafer image is of size $N_x \times N_y$ in pixels. Let the complexity required to process this image be C.

Figure 3B:
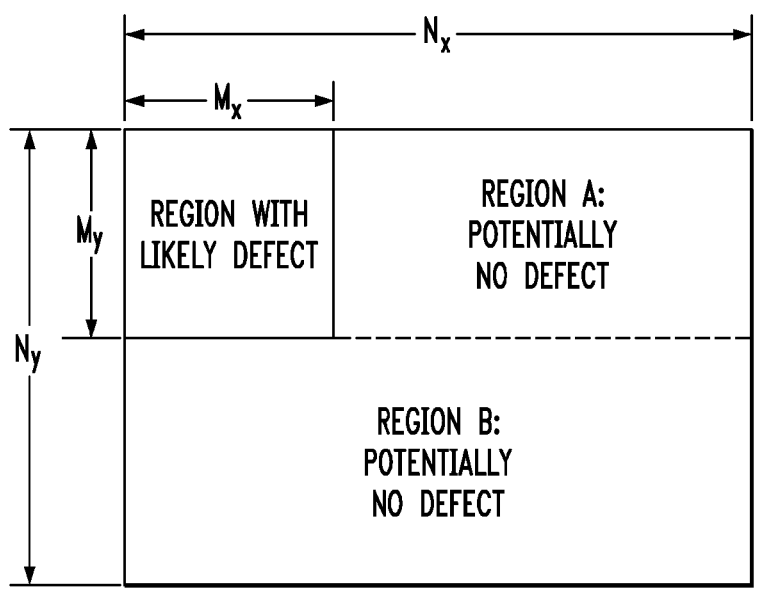
FIG. 3B illustrates potential defect regions in an image identified by tool trace analysis, according to an embodiment of the invention.

Consider now that using the tool trace analysis, potential defects are identified in a sub-region of the image with size $M_x \times M_y$ (and no defects are detected in other regions), as shown in FIG. 3B. Then the morphological analysis may be applied at full resolution only in the region of interest (the region marked likely to have defect) and may be applied at lower resolution in the other regions of the image. Hence, sub-regions A and B, with no defect may be processed at lower resolution by sub-sampling with factor k (without impacting accuracy) in each direction. The resulting complexity needed to process the image is:

$$\frac{C}{N_x N_y}\left[M_x M_y + \frac{(N_x - M_x)M_y}{k^2} + \frac{(N_y - M_y)N_x}{k^2}\right].$$

In the summation above, the first term corresponds to the number of pixels in the region with likely defect, the second term corresponds to the number of pixels in Region A (at a reduced resolution) and the third term corresponds to the number of pixels in Region B (at reduced resolution). As a numerical example, consider that $N_x=N_y=1000$, $M_x=M_y=100$ and k=4. In this case the resulting complexity is 0.0719 C, resulting in complexity savings by over a factor of 14.

Figure 4A:
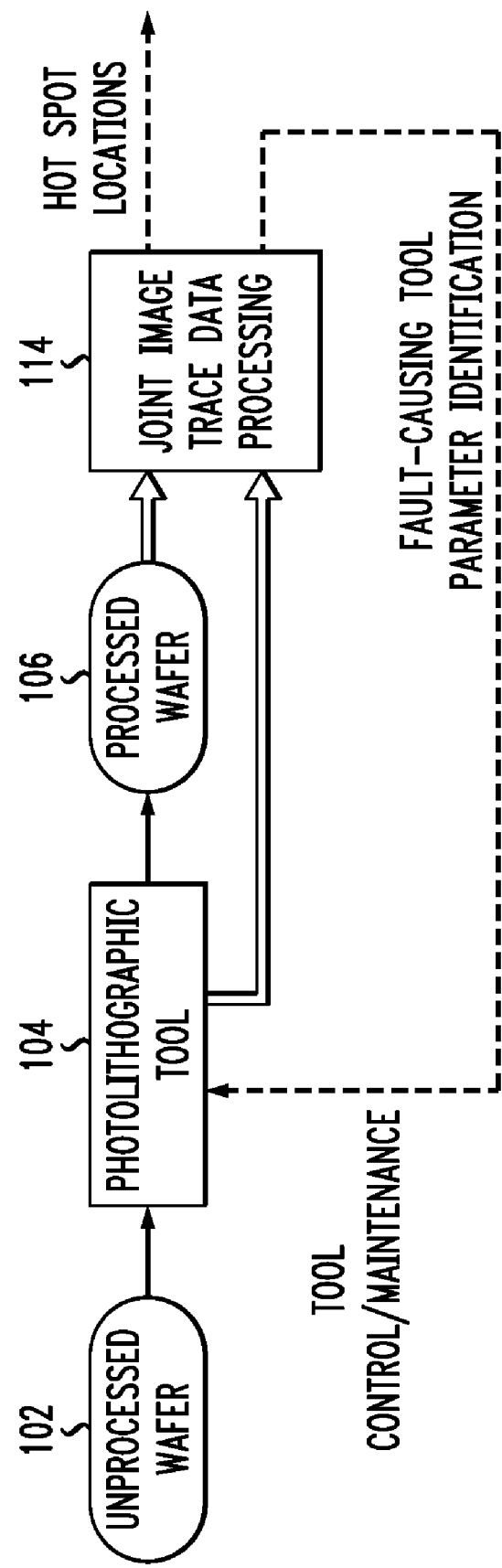
FIG. 4A illustrates a multi-modal data analysis methodology for performing joint analysis of wafer image and tool trace data, according to an embodiment of the invention.

FIG. 4A illustrates a multi-modal data analysis methodology for performing joint analysis of wafer image and tool trace data, according to an embodiment of the invention. By jointly analyzing the wafer image data and tool trace data in joint image trace data processing unit 114, we can not only detect the wafer defects more accurately, but we can then further also correlate these defects with the underlying tool trace parameters to identify potential causes for defect creation, in terms of out-of-specification parameters, perturbed parameters, etc.

We can also use this joint analysis to determine the sensitivity of the wafer defect to the different parameters, and determine appropriate control limits for them. Using these control limits, we can also implement an automated and dynamic fault detection and classification system for the photolithographic tool (an example of a controllable process), as illustrated by the feedback system in FIG. 4A. Note though that this joint analysis may require computation intensive operations that may be partitioned, using a stream processing paradigm, into a set of hierarchical and adaptive steps to trade off computational resources and prediction accuracy dynamically. That is, both the trace data as well as the images may be processed using a stream processing paradigm where computation is partitioned into a set of hierarchical steps, where low complexity processing is used to filter out as much irrelevant information as possible, such that high complexity (and high accuracy) processing can be performed on a reduced and relevant sub-set of the data.

Thus, as shown, processing unit 114 jointly performs the image analysis and tool trace analysis tasks and outputs hot spot locations and identifies fault-causing tool parameter(s) that can be used to automatically and/or manually control/maintain photolithographic tool 104.

Furthermore, joint analysis of the tool trace data and the wafer images may be performed using "early fusion" techniques from classification theory. In this case, the data is examined jointly, and any models are constructed on the combined data set. A significant advantage of this is in terms of capturing very efficiently the cross correlations across the data sets (in this case, the trace data and the wafer images) and being able to improve accuracy significantly (under the availability of sufficient amount of data to avoid the problem of dimensionality).

Consider a simple example with two classifiers where classifier i bases its classification decision on a measurements $X_i$. Consider that the feature space consists of data from two classes (defective wafers and non-defective wafers). Consider an example of the data distribution shown in FIG. 4B, with light grey stars corresponding to defective wafers and dark grey stars corresponding to non-defective wafers. The goal of the classification is to detect the defective wafers.

Figure 4B:
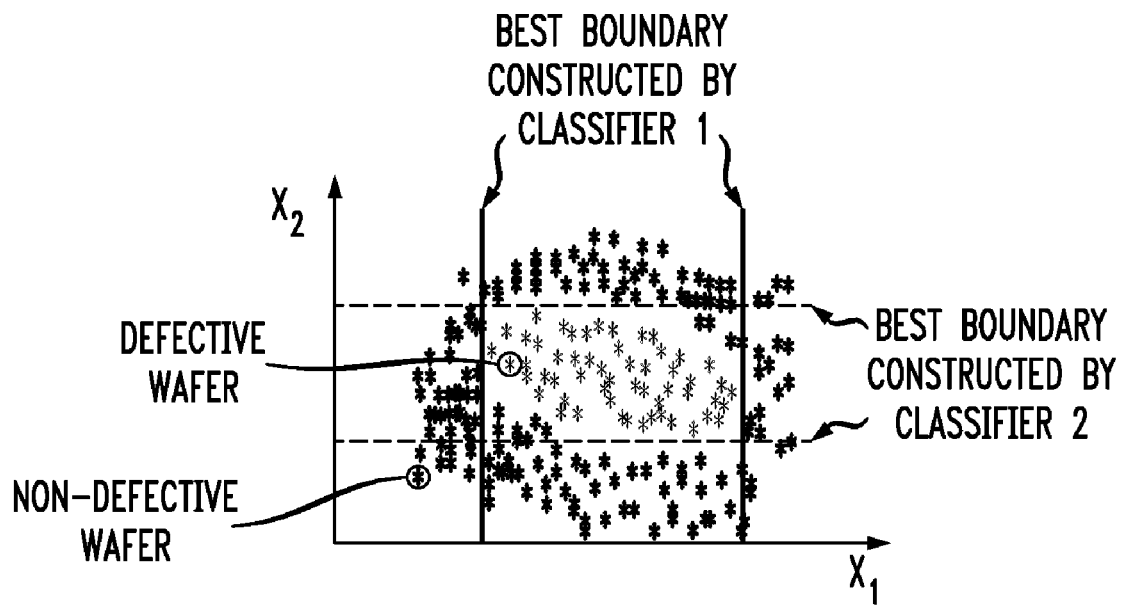
FIG. 4B illustrates distribution of data and best classification from individual classifiers, according to an embodiment of the invention.
Figure 4C:
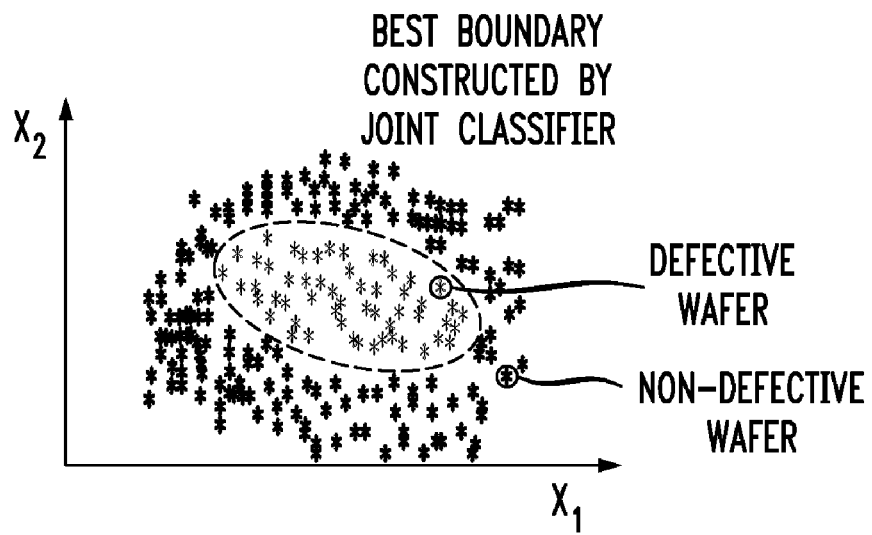
FIG. 4C illustrates early fusion and joint analysis for no mistakes with perfect detection, according to an embodiment of the invention.

As shown in FIG. 4B, the best each individual classifiers (using only one variable, $x_1$ or $x_2$) can do is shown by the vertical and horizontal boundaries. In either case, several mistakes are made (i.e. a lot of dark grey stars or non-defective wafers lie within the boundary shown) while detecting defective wafers. If result fusion were used, i.e., the two classifiers operate independently and only classification results of the two classifiers were combined: in this case, the resulting boundary would be the rectangle formed by the two horizontal and vertical lines, which reduces some of the errors, but still has some errors. Instead, if the two variables $x_1$ and $x_2$ are jointly considered (as in early fusion) by one classifier, then the correlation between the two can easily be exploited to determine an elliptical decision boundary that captures only the defective wafers while making no mistakes. This is shown in FIG. 4C.

Referring lastly to FIG. 5, a computer system is illustrated wherein techniques for performing joint multi-modal analysis may be implemented according to an embodiment of the invention. That is, FIG. 5 illustrates a computer system in accordance with which one or more components/steps of the analysis techniques (e.g., components and methodologies described above in the context of FIGS. 1 through 4) may be implemented, according to an embodiment of the invention.

It is to be understood that the individual components/steps may be implemented on one such computer system or on more than one such computer system. In the case of an implementation on a distributed computing system, the individual computer systems and/or devices may be connected via a suitable network, e.g., the Internet or World Wide Web. However, the system may be realized via private or local networks. In any case, the invention is not limited to any particular network.

Thus, the computer system shown in FIG. 5 may represent tool trace analyzer 108, wafer image analyzer 110, result fusion unit 112, and joint image trace data processing unit 114 described herein.

As shown, computer system 500 includes processor 502, memory 504, input/output (I/O) devices 506, and network interface 508, coupled via a computer bus 510 or alternate connection arrangement.

It is to be appreciated that the term "processor" as used herein is intended to include any processing device, such as, for example, one that includes a CPU and/or other processing circuitry. It is also to be understood that the term "processor" may refer to more than one processing device and that various elements associated with a processing device may be shared by other processing devices.

The term "memory" as used herein is intended to include memory associated with a processor or CPU, such as, for example, RAM, ROM, a fixed memory device (e.g., hard drive), a removable memory device (e.g., diskette), flash memory, etc. The memory may be considered a computer readable storage medium.

In addition, the phrase "input/output devices" or "I/O devices" as used herein is intended to include, for example, one or more input devices (e.g., keyboard, mouse, etc.) for entering data to the processing unit, and/or one or more output devices (e.g., display, etc.) for presenting results associated with the processing unit.

Still further, the phrase "network interface" as used herein is intended to include, for example, one or more transceivers to permit the computer system to communicate with another computer system via an appropriate communications protocol.

Accordingly, software components including instructions or code for performing the methodologies described herein may be stored in one or more of the associated memory devices (e.g., ROM, fixed or removable memory) and, when ready to be utilized, loaded in part or in whole (e.g., into RAM) and executed by a CPU.

In any case, it is to be appreciated that the techniques of the invention, described herein and shown in the appended figures, may be implemented in various forms of hardware, software, or combinations thereof, e.g., one or more operatively programmed general purpose digital computers with associated memory, implementation-specific integrated circuit(s), functional circuitry, etc. Given the techniques of the invention provided herein, one of ordinary skill in the art will be able to contemplate other implementations of the techniques of the invention.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A method for identifying one or more defects in a wafer produced by a photolithography process, the method comprising steps of:
    obtaining tool trace parameter data generated as a result of production of the wafer in accordance with a photolithography tool, wherein at least a portion of the tool trace parameter data comprises data representing an existence of a pressure differential in a measured back side pressure of the wafer;
    obtaining after development inspection (ADI) image data generated as a result of inspection of the wafer;
    analyzing the tool trace parameter data such that image processing analysis of the ADI image data to detect one or more hot spots on the wafer is performed at a high resolution only in regions of the wafer that exhibit a given pressure differential; and
    identifying one or more defects in the wafer at the one or more detected hot spots.

* * * * *